(12) United States Patent
Lochmann et al.

(10) Patent No.: US 12,274,795 B2
(45) Date of Patent: Apr. 15, 2025

(54) COATING MATERIAL FOR USE IN AN HMC METHOD

(71) Applicant: IOI OLEO GMBH, Hamburg (DE)

(72) Inventors: Dirk Lochmann, Deutschland (DE); Sebastian Reyer, Deutschland (DE); Michael Stehr, Deutschland (DE); Andreas Zimmer, Osterreich (AT); Sharareh Salar Behzadi, Osterreich (AT)

(73) Assignee: IOI OLEO GMBH, Hamburg (DE)

( * ) Notice: Subject to any disclaimer, the term of this patent is extended or adjusted under 35 U.S.C. 154(b) by 423 days.

(21) Appl. No.: 17/276,177

(22) PCT Filed: Oct. 22, 2018

(86) PCT No.: PCT/DE2018/000302
§ 371 (c)(1),
(2) Date: Mar. 15, 2021

(87) PCT Pub. No.: WO2020/083411
PCT Pub. Date: Apr. 30, 2020

(65) Prior Publication Data
US 2021/0361587 A1    Nov. 25, 2021

(51) Int. Cl.
*A61K 9/50* (2006.01)
*A61K 31/198* (2006.01)
*B05B 7/16* (2006.01)

(52) U.S. Cl.
CPC .......... *A61K 9/5015* (2013.01); *A61K 9/5089* (2013.01); *A61K 31/198* (2013.01); *B05B 7/1606* (2013.01)

(58) Field of Classification Search
CPC ... A61K 9/5015; A61K 9/5089; A61K 9/5078
See application file for complete search history.

(56) References Cited

U.S. PATENT DOCUMENTS 5,162,057 A * 11/1992 Akiyama ............. A61K 9/5078
106/217.7
5,891,476 A * 4/1999 Reo ....................... A61K 9/0056
424/498

(Continued)

FOREIGN PATENT DOCUMENTS

EP    0451461    * 10/1991    ............ A61K 47/14
EP    0451461 A2    10/1991

(Continued)

OTHER PUBLICATIONS

Becker2 et al., Solvent-Free Melting Techniques for the Preparation of Lipid-Based Solid Oral Formulations, 2015, Pharm Res, vol. 32, pp. 1519-1545 (Year: 2015).*

(Continued)

*Primary Examiner* — Dah-Wei D. Yuan
*Assistant Examiner* — Andrew J Bowman
(74) *Attorney, Agent, or Firm* — Miles & Stockbridge PC; Ajay A. Jagtiani

(57) ABSTRACT

The invention relates to a coating material for use in a hot-melt coating method, said material containing as the main constituent one or more polyglycerol fatty acid, each obtained by way of a complete or partial esterification of a linear or branched polyglycerol containing two to eight glyceryl units with one or more fatty acids, each containing 6 to 22 carbon atoms.

15 Claims, 8 Drawing Sheets

(56) References Cited

U.S. PATENT DOCUMENTS

2004/0043070 A1*  3/2004  Ayres ............... A61K 9/5089
                                                       424/471
2010/0092569 A1   4/2010  Lorenzon

FOREIGN PATENT DOCUMENTS

| EP | 2198859 A1 * | 6/2010 | ............ A61K 9/501 |
| WO | 2011110926 A1 | 9/2011 | |
| WO | WO2011100926 * | 9/2011 | ............... A23C 9/12 |
| WO | WO-2014167124 A1 * | 10/2014 | ........... A61K 31/198 |

OTHER PUBLICATIONS

Lopes et al., Role of Lipid Blooming and Crystallite Size in the Performance of Highly Soluble Drug-Loaded Microcapsules, 2015, Pharmaceutics Drug Delivery and Pharmaceutical Technology, vol. 104, pp. 4257-4265 (Year: 2015).*
International Search Report and Written Opinion dated Jul. 19, 2019 in corresponding International Application No. PCT/DE2018/000302.
Becker, Karin et al., "Solvent-Free Melting Techniques for the Preparation of Lipid-Based Solid Oral Formulations," Pharmaceutical Research, Mar. 19, 2015, pp. 1519-1545, vol. 32, No. 5, Springer, NY, US.
Lopes, D.G., et al., "Designing Optimal Formulations for Hot-Melt Coating," International Journal of Pharmaceutics, 2017, pp. 357-363, vol. 533, No. 2.
Lopes, D.G., et al., "Role of Lipid Blooming and Cyrstallite Size in the Performance of Highly Soluble Drug-Loaded Microcapsules," Journal of Pharmaceutical Sciences, 2015, pp. 4257-4265, vol. 104.

* cited by examiner

COATING MATERIAL FOR USE IN AN HMC METHOD

CROSS-REFERENCE TO RELATED APPLICATIONS

This application is a National Stage of International Application No. PCT/DE2018/000302 filed on Oct. 22, 2018, which is hereby incorporated by reference in its entirety.

Compositions for coating material for use in a hot-melt coating method, HMC method for short, which can also be used in the production of pharmaceuticals, are presented.

HMC methods offer advantages over other coating methods. In an HMC method, disperse material, for example solid particles in a gas or gas mixture as dispersant, is sprayed with the coating material, the disperse material usually being provided as a fluidized bed. Disperse material designates here material that is separated from the surrounding medium by a phase interface. In contrast to other methods, the viscosity of melted HMC coatings is low enough for the method step of spraying, so that the use of solvents, such as for example water, to reduce the viscosity is unnecessary. Thereby also energy-consuming and time-consuming drying steps can be dispensed with. The risk that the disperse material undesirably dissolves partially in the coating material during the coating method is also significantly reduced with solvent-free HMC coatings. The HMC method is already frequently used in the food industry. For the production of pharmaceuticals, the coating of granulates, crystals or generally particles, more generally also including liquid droplets, for example, of disperse material which has one or more pharmaceutical active ingredients is frequently required in order to mask, for example, unpleasant taste, to protect the active ingredient from environmental influences, such as moisture or UV radiation for example, or to influence the rate of active ingredient release. In order to be able to also use HMC methods in pharmaceutical production, the HMC coatings must fulfil particular requirements. In particular, they must remain stable over a lengthy period of time and their physicochemical properties should only change within very narrow limits as far as possible over a period of years, in order to be able to guarantee constant release kinetics of the pharmaceutical active ingredient or a sufficient protection in the case of prolonged storage. Any method in which disperse material is coated with solvent-free coating material by spraying the coating material as a melt is designated here as hot-melt coating or HMC method, the size of the individual parts of the disperse material basically being freely selectable. The coating material used here is also designated below as HMC coating or HMC coating material.

Various HMC coatings are known in the meantime, which were mostly developed for particular pharmaceutical active ingredients. WO 2014/167124 A1 explicitly names the problem that triglycerides, such as glycerol tripalmitate or glycerol tristearate, have polymorphisms, therefore respectively are present both in a crystalline, unstable α-modification and also in a metastable ß'-modification or a stable ß-modification, and can pass from one into the other modification. The modifications differ here in particular through the thickness of lamellar-packed, crystalline subunits, which are also designated as subcellular units. For the α-modification of glycerol tristearate, for example, a stratification of on average 6 lamellar structures per subcellular unit was able be determined under certain conditions, after complete transfer into the ß-modification then a stratification of on average 10.5 lamellar structures per subcellular unit and an increase in crystal thickness of about 67%. The tact that the mathematically to be expected increase of 75 is not achieved is probably due to the fact that the individual lamellae of the ß-modification have a denser lamellar packing, due to an inclination occurring compared to the α-modification (see D. G. Lopes, K. Becker, M. Stehr, D. Lochmann et al. in Journal of Pharmaceutical Sciences 104: 4257-4265, 2015). Since the α-modification has a faster formation kinetics than the ß'- and the ß-modification at the temperatures which are kept as low as possible during spraying in the HMC method, the α-modification is present after completed coating of active substance-containing disperse material by means of the HMC method which, however, undesirably rearranges itself into the more stable ß-modification during storage under the increase in volume of the coating known as "blooming", which is also associated with macroscopic breaks. The solution to the problem which is discussed takes place according to WO 2014/162124 A1 through the addition of a polysorbate, therefore a nonionic surfactant, wherein the polysorbate component is 10-30% of the coating material. The mixture of triglyceride and polysorbate in fact no longer appears to have the problem of "blooming", but can separate out in the long term, so that a change in the release kinetics, which should be basically stable in pharmaceutical formulations, cannot be ruled out.

U.S. Pat. No. 5,891,476 discloses a composition with carnauba wax, which is to have no polymorphism. However, the high melting temperatures for carnauba wax, which lie between 82° C. and 86° C., are disadvantageous. The compositions which are disclosed are therefore unsuitable for thermolabile active ingredients, since the temperatures in the HMC method would have to be partly 100° C. or more, with the additional disadvantage that the wax, solidifying very quickly when the temperature decreases, easily settles in the lines and nozzles of the HMC device, and in so doing causes blockages in the device.

US 2010/0092569 A1 discloses the embedding of a silicate powder adsorbate of an active ingredient into a molten lipid matrix with subsequent spraying and cooling for the production of coated particles, wherein the lipid matrix consists of triglycerides of saturated even-numbered fatty acids each having 16 to 22 carbon atoms and 3% of an emulsifier, which is to ensure the homogeneity of the dispersion of the active ingredient in the lipid matrix. This production method also requires temperatures above 70° C. and is therefore unsuitable for temperature-sensitive active ingredients. The disclosed method serves for the production of an animal food; the release kinetics of the active ingredient, which are critical for medicinal products for human use, are not addressed in the named publication.

Against this background, the problem of posed of providing a coating material for an RMC method and disperse material coated with a coating which does not have the previously discussed disadvantages of the prior art, as well as an HMC method which is also suitable for the coating of disperse material which has one or more pharmaceutical active ingredients, for which a composition of a coating material is used, which desirably does not have mixture separations either before or after the coating of the composition which is used, does not show any modification changes due to polymorphism which are accompanied by a change in the volume of the coating, and if necessary in addition ensures stable release kinetics and in so doing, if necessary, can also be processed together with disperse material which has thermolabile pharmaceutical active ingredients. A pharmaceutical active ingredient is understood here to mean a substance which is able to be used as a pharmacologically active component of a medicament. Substances here are chemical elements and chemical compounds as well as their naturally occurring mixtures and solutions, plants, parts of plants, plant components, algae, fungi and lichens in processed or unprocessed state, animal bodies, also live animals, as well as body parts, body components and metabolic products of humans or animals in processed or unprocessed state, microorganisms including viruses as well as their components or metabolic products. Pharmaceuticals here are substances or preparations made of substances which are intended for use in or on the human or animal body and are intended as agents with properties for curing or relieving or for preventing human or animal diseases or pathological ailments or which can be used in or on the human or animal body or can be administered to a human or animal to either restore, correct or influence the physiological functions through a pharmacological, immunological or metabolic effect or to make a medical diagnosis. Objects that contain a medicament in the above sense or to which a medicament in the above sense is applied and which are intended to be brought into permanent or temporary contact with the human or animal body, as well as substances and preparations of substances which, also in interaction with other substances or preparations of substances, are intended to be used without being used on or in the animal body, to indicate the constitution, state or function of the animal body or to serve to reveal pathogens in animals, are also deemed to be medicaments here.

The above-mentioned problem is solved by a coating material according to claim 1, a combination of disperse material and such coating material according to claim 14 and a hot-melt coating method according to claim 12, wherein advantageous embodiment variants result from the respective subclaims.

The accompanying drawings, which are incorporated herein and constitute part of this specification, illustrate exemplary embodiments of the invention, and, together with the general description given above and the detailed description given below, serve to explain the features of the invention.

Figure 11:
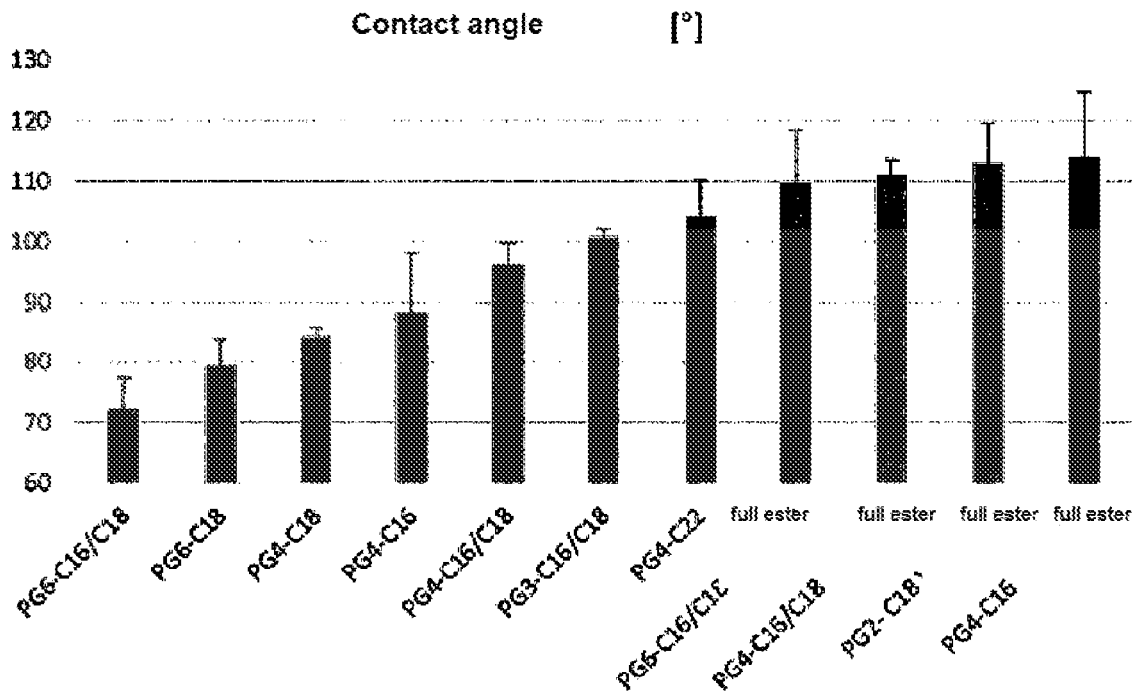

FIG. 11 graphically illustrates PG(4)-C18 partial ester assigned to the more hydrophilic polyglycerol fatty acid esters according to one embodiment of the present disclosure.

Figure 12:
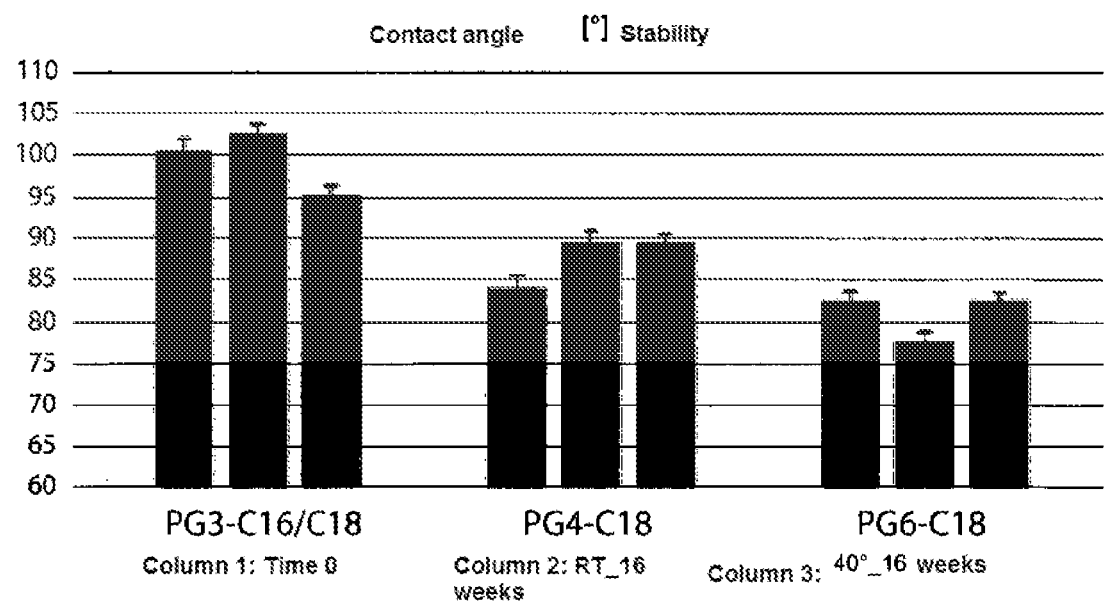

FIG. 12 illustrates the change in the contact angle for PG(4)-C18 partial esters (middle diagram) compared to the start measurement (left column) after 16 weeks at room temperature (middle column) and after 16 weeks at 40° C. (right column) and similarly applied to PG3-C16/C18 partial esters (left diagram) and PG6-C18 partial esters (right diagram) according to one embodiment of the present disclosure.

Figure 13:
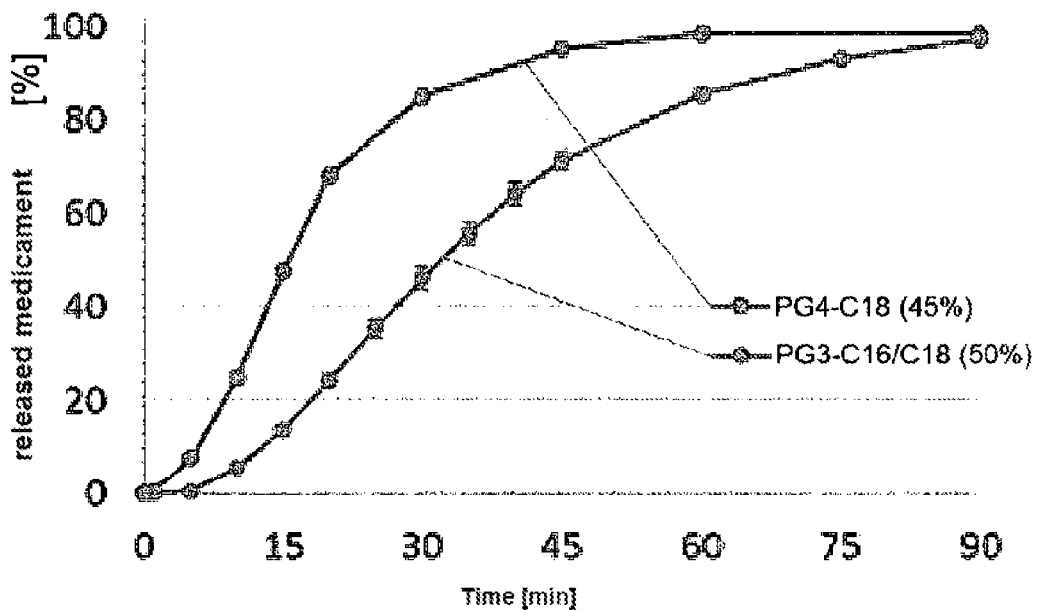

FIG. 13 illustrates the release kinetics for particles coated with PG(4)-C18 partial esters and alternatively with PG (3)-C16/C18 partial esters, each with 600 mg of N-acetylcysteine according to one embodiment of the present disclosure.

Figure 14:
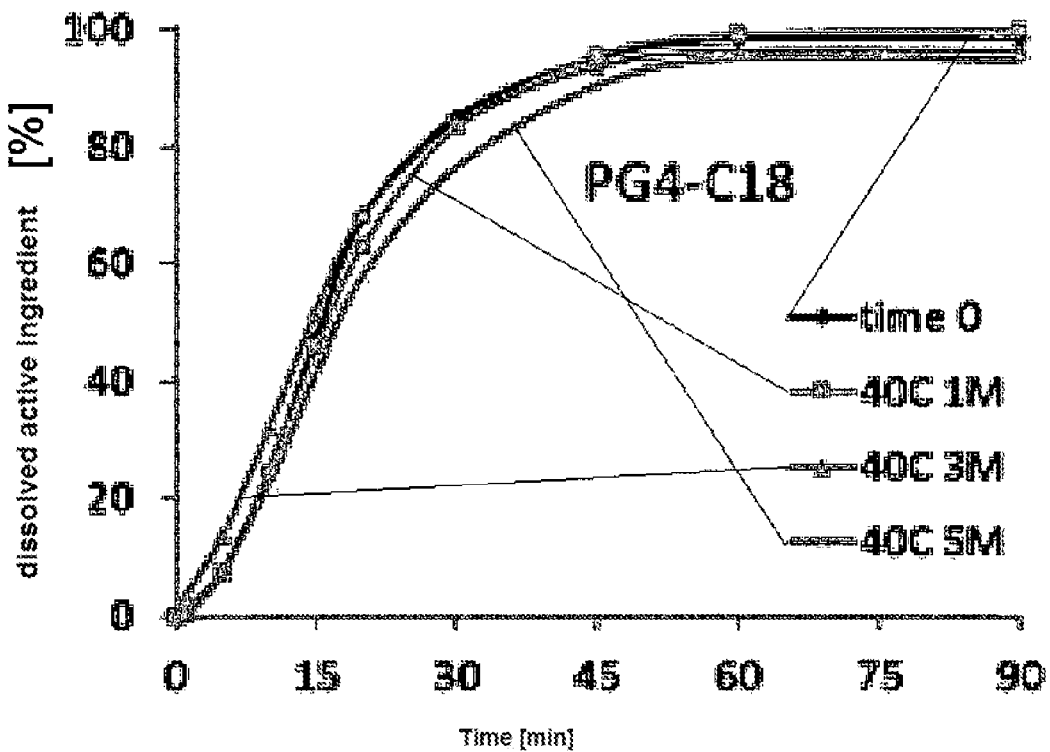

FIG. 14 illustrates the release kinetics of the N-acetylcysteine particles coated with PG(4)-C18 partial ester at the beginning, after one month, three months and five months of storage at 40° C. according to one embodiment of the present disclosure.

Figure 15:
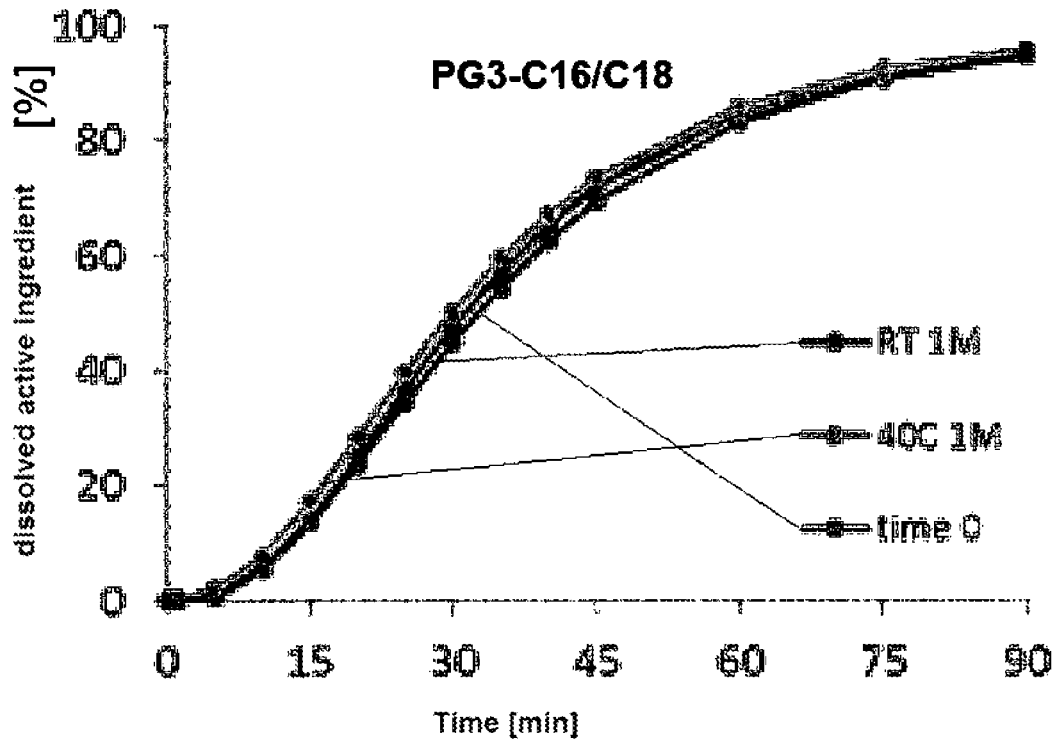

FIG. 15 illustrates the release kinetics of the N-acetylcysteine particles coated with PG (3)-C16/C18 partial ester at the beginning, after storage for one month at room temperature and after storage for one month at 40° C. according to one embodiment of the present disclosure.

Figure 16:
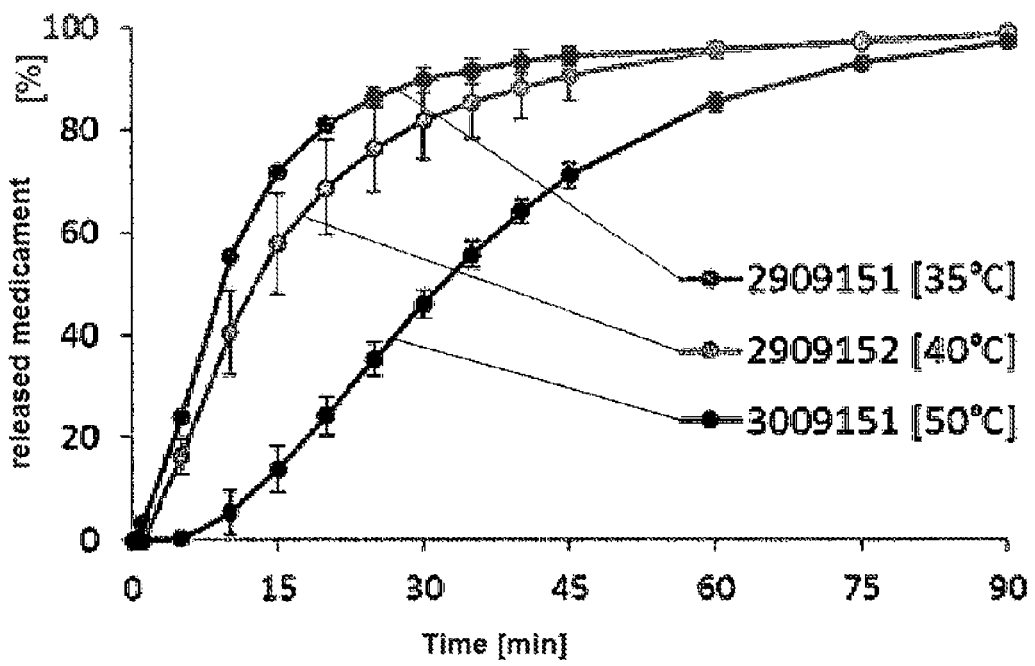

FIG. 16 illustrates the release curves for the particles coated with an air inlet temperature of 35° C., 40° C. and 50° C. in the HMC method according to one embodiment of the present disclosure.

A coating material is proposed for use in a hot-melt coating method, which contains as the main constituent one or more polyglycerol fatty acid esters, each obtained by way of a complete or partial esterification of a linear or branched polyglycerol containing two to eight glyceryl units with one or more fatty acids, each containing 6 to 22 carbon atoms. The main constituent means here that polyglycerol fatty acid esters make up the highest percentage proportion by weight of the proposed coating material. The proposed coating material preferably consists of polyglycerol fatty acid esters or post-synthetic mixtures of these, apart from synthesis-related accompanying substances, which can make up to two percent by weight.

The simplest polyglycerols that can be used as starting materials for the intended esterification are linear and branched diglycerols with the empirical formula C which are synthetically provided industrially in a known manner, for example by reacting glycerol with 2,3-epoxy-1-propanol under base catalysis with the formation of ether bonds, or by thermal condensation under base catalysis, wherein the reaction containing mainly diglycerols can subsequently be separated.

Diglycerols can occur in three different structural isomeric forms, namely in the linear form, in which the ether bridge is formed between the respective first carbon atoms of the two glycerol molecules employed, in the branched form, in which the ether bridge is formed between the first carbon atom of the first and the second carbon atom of the second glycerol molecule employed, and in a nucleodendrimeric form, in which the ether bridge is formed between the respective second carbon atoms. In the case of the condensation of two glycerol molecules catalysed by an alkali, up to approximately 80% occurs in the linear form and up to approximately 20% in the branched form, while only a very small quantity of the nucleodendrimeric form is produced.

Likewise for the intended esterification with fatty acids, polyglycerols containing more than two and up to eight glyceryl units may be used. In general, the polyglycerols are abbreviated to "PG" and provided with an integer n as a subscript, which provides the number of polyglyceryl units, therefore "$PG_n$". As an example, triglycerols would be indicated as $PG_3$ and would have the empirical formula $C_9O_7H_{20}$. The complete esterification with a fatty acid, for example with stearic acid, would now take place at all of the free hydroxyl groups of the PG-molecule, in the case of a linear $PG_3$ therefore at the first and second carbon atom of the first glyceryl unit, at the second carbon atom of the second glyceryl unit and at the second and third carbon atom of the third glyceryl unit. The empirical formula for this example would therefore be indicated as $C_9O_7H_{15}R_5$, wherein each R would represent a fatty acid residue, in the selected example with the empirical formula $C_{18}OH_{35}$.

For the abbreviation of polyglycerols esterified with saturated unbranched fatty acids, however, the designation PG(n)-Cm full ester or, as appropriate, PG(n)-CM partial ester, has become established, wherein the "n" in parenthesis, in similar manner to the designation of the polyglycerols, indicates the number of glyceryl units contained in the molecule and m represents the number of carbon atoms of the saturated fatty acid used for the esterification reaction. Thus, the n represents the number of glyceryl units with the empirical formula $C_3O_2H_5R$, or respectively $C_3O_3H_5R_2$ for marginal glyceryl units, wherein R may represent a fatty acid residue or the hydrogen atom of a free hydroxyl group. PG(2)-C18 full ester would therefore designate polyglycerol fatty acid full ester with the empirical formula $C_{78}O_9H_{150}$. In the case of the PG-partial esters, the number of fatty acid residues is averaged, wherein at the same time, the empirical formula indicates the fraction with the esterification variants which are most frequently present. A more exact designation for the polyglycerol fatty acid partial esters is provided by the additional indication of the hydroxyl value, which is a measure of the non-esterified hydroxyl group content and thus provides information regarding the degree of esterification of the partial ester. Presumably for steric reasons, the esterification reactions in this case occur preferentially from the outside to the inside. Thus, initially, the hydroxyl groups which are esterified are those which allow the fatty acid residue the highest degree of freedom. The first esterification reaction at a linear polyglycerol accordingly preferentially takes place at the hydroxyl group of the first carbon atom of a marginal polyglyceryl unit, then the second esterification reaction takes place at the hydroxyl group of the third carbon atom of the marginal polyglyceryl unit at the other end. Next, the hydroxyl groups at carbon positions immediately adjacent to positions which have already been esterified are esterified, and so on.

Fatty acids are understood here to mean aliphatic monocarboxylic acids containing 6 to 22 carbon atoms, which are preferably unbranched and saturated and have an even number of carbon atoms, but they may also be odd-numbered, branched and/or unsaturated. Particularly preferably, for the preparation of the proposed polyglycerol fatty acid esters, unbranched, saturated fatty acids containing 16, 18, 20 or 22 C-atoms are used, therefore palmitic, stearic, arachidic or behenic acid.

Surprisingly, the proposed polyglycerol fatty acid esters, in contrast to monoglycerol fatty acid esters, such as for example triacylglycerols, show no polymorphism. The polyglycerol fatty acid esters, each individually examined by means of dynamic differential calorimetry, have only an endothermic minimum for the heat flow, which is indicated in mW/g, during the heating up, which occurs due to the melting of the examined sample, and only an exothermic maximum during the cooling that occur s due to the solidification of the examined sample. In contrast thereto, in the examination of triacylglycerols having polymorphism, different local minima are found, namely when the sample is heated up, a first local endothermic minimum when the α-modification melts, followed by a local exothermic maximum during crystallization to the more stable ß-modification, which is indicated by a further local endothermic minimum of the heat flow, which also melts as the temperature increases further. The temperature changes during heating up and cooling down take place here evenly over time. No additional endothermic or exothermic transitions are observed during a storage at room temperature or at 40° C. over 6 months.

Individual examinations of the proposed polyglycerol fatty acid esters below their respective solidification temperature by means of wide-angle X-ray scattering, abbreviated to "WAXS", show an intensity maximum for all examined polyglycerol fatty acid esters, which indicates a deflection angle of respectively 21.4°, corresponding to about 2q, therefore twice the Bragg angle, from which there results a spacing of the network planes of 415 pm, which correlates here with the lamellar packing density of the examined molecules. This distance can be structurally assigned to the α-modification, in which the respective lamellar structures are arranged parallel to one another in a hexagonal lattice with plane-forming molecules which are stacked on top of one another. No other modifications can be identified. The stability of the identified α-modification was also observed by means of WAXS both at room temperature and at 40° C. over respectively 6 months. Here too, exclusively the surprisingly stable α-modification was found respectively for the examined polyglycerol fatty acid esters.

A further confirmation that the proposed polyglycerol fatty acid esters have no polymorphism is provided by the individual analysis of the widest variety of polyglycerol fatty acid esters by means of small-angle X-ray scattering, abbreviated to SAXS. SAXS allows conclusions to be drawn about the size, shape and inner surface of crystallites. The thickness of the respective crystallites can be calculated here by means of the Scherrer formula, according to which $D=K\lambda/FWHM \cos(\theta)$ applies. D denotes here the thickness of the crystallite and K the dimensionless so-called Scherrer constant, which allows statements about the shape of the crystallite and can usually be assumed to be 0.9 in good approximation. FWRM stands for "full width at half maximum", therefore for the width of the peak of an intensity maximum at half height compared to the background measured in radians (rad) and 9 is the Bragg angle, therefore the angle of incidence of the radiation onto the network plane. While a sample, known from the prior art, of glycerol tripalmitate stabilized with 10% polysorbate 65 after six months of storage at room temperature has a crystallite thickness of 0.31 nm, corresponding to seven lamellae, and its crystallite thickness after six months of storage at 40° C. at 52 nm, corresponding to 12 lamellae, is almost doubled, the proposed polyglycerol fatty acid partial esters show mostly crystallite thicknesses of 20 to 30 nm, corresponding to 2 to 4 lamellae, and are stable in unchanged modification after six months of storage at 40° C. In contrast, polyglycerol full esters mostly show a slightly increased crystallite thickness of 30 to 40 nm, corresponding to 5 to 5 lamellae, indicating a higher degree of organization, and are likewise stable in unchanged modification after storage for six months at 40° C.

The following polyglycerol fatty acid full esters are preferred for use in or as HMC coating material: PG(2)-C18, PG(2)-C22, PG(3)-C22, PG(4)-C16 and PG(4)-C16/C18 and PG(6)-C16/C18, respectively with a C16 complementary to 100 to C18-ratio of 35 to 45 to 55 to 65, preferably 40 to 60. Full esters from this group have melting points below 80° C., apart from PG(2)-C22 and PG(3)-22 even below 60°, and are therefore readily well-suited for HMC methods, especially since their solidification point, which is also decisive for the method, lies approximately 3° to 7° below the respective melting point. The same applies to the following polyglycerol fatty acid partial esters, wherein in the following the respectively preferred range for the typical average hydroxyl number in the first square bracket and the respectively particularly preferred typical average hydroxyl number in the second square bracket are appended to the designation: PG(2)-C22-[15-100]-[17], PG(3)-C22-[100-200]-[137], PG(4)-C16 [150-250]-[186], PG(4)-C18 [100-200]-[163], PG(4)-C22-[100-200]-[145], PG(6)-C18-[100-200]-[133] and PG(3)-C16/C18-[100-200]-[148], PG(4)-C1/C18-[150-250]-[187], PG(6)-C16/C18-[200-300]-[237], respectively with a C16 to C18 ratio of 40 to 60. The named partial esters also have melting points below 80° C., apart from PG(2)-C22 partial esters, PG(3)-C22 partial esters and PG(4)-C22 partial esters even below 60° C., wherein the solidification points, as with the full esters, are about 3° C. to 7° C. below the respective melting points.

So that the proposed polyglycerol fatty acid esters are suitable for an HMC method, their viscosity at 80° C. should be less than 300 mPa·s, preferably less than 200 mPa·s and particularly preferably less than 100 mPa·s, since the usually used atomizing nozzles for the melted coating material would clog too easily at higher viscosities. The limit of a melting temperature of the coating material of 80° C. should only be exceeded in exceptional cases, since the process control temperatures then overall have to be set too high for sensitive pharmaceutical substances.

Preferably, those of the proposed polyglycerol fatty acid esters are used for an HMC method in which the solidification temperature is below 75° C., particularly preferably between 43° C. and 56° C., since the Low process control temperatures that are possible therewith are to be aimed for already for reasons of energy consumption, process reliability and the larger selection with regard to the disperse material that is able to be used. The solidification temperature is defined here as the temperature value at which the maximum of the highest exothermic peak of the heat flow occurs on cooling during a sample analysis by means of dynamic differential calorimetry.

For the selection of a proposed polyglycerol fatty acid ester suitable for the disperse material which is to be coated, its hydrophobicity is important, since this is associated with the wettability, which, like the water absorption capacity and the erosion behaviour of the coating material has an influence on the release kinetics of the coated disperse material. The hydrophobicity is determined by determining the contact angle between the coating material in the solid aggregate state and a drop of purified water. According to Young's equation, $\cos \theta = (\gamma_{Sv} - \gamma_{SL})/\gamma_{LV}$, where $\gamma_{SL}$ is the interfacial tension between coating material and water, $g_{LV}$ is the surface tension of the water drop and $\gamma_{Sv}$ is the interfacial tension between coating material and ambient air. $\theta$ is the contact angle. The larger the contact angle $\theta$ therefore, the greater also the interfacial tension between coating material and water and the higher the hydrophobicity of the examined coating material. The contact angles for the proposed polyglycerol fatty acid esters also correlate with the HLB value customary in pharmaceutical technology, which provides information on a scale from 0 to 20 about the ratio of lipophilic to hydrophilic molecular parts, wherein the hydrophilic part increases with increasing HLB value. The contact angle of the coating material under storage conditions should be subject to only moderate changes for processing one or more disperse materials containing pharmaceutical active ingredients by means of the HMC method, so that the stability of the release kinetics of the active pharmaceutical ingredient or ingredients is ensured. The polyglycerol fatty acid esters are therefore preferably used as the main constituent of the coating material, the contact angle of which, at 40° C. as well as at 20° C. after 16 weeks has less than 10° deviation from the initial value. At 40°, the deviation of the contact angle under the named conditions for glycerol tristearin would be comparatively high and thus detrimental to a desirable constancy of the release kinetics, for example, which is due to a rearrangement during storage from the α- to the ß-modification.

Basically, it is sufficient for the provision of a proposed coating material if this, apart from synthesis-related impurities, which should not be more than two percent by weight, consists of polyglycerol fatty acid esters which are obtainable from esterification reactions, all of which are carried out with the same reactants. In order to make fine adjustments to the properties of the coating material, however, it is also possible to post-synthetically mix with one another polyglycerol fatty acid esters which can be obtained from esterification reactions which differ from one another owing to different reactants, in so far as no separation occurs. Neutral admixtures to the polyglycerol fatty acid esters used for the coating material are also possible, in so far as polyglycerol fatty acid esters remain the main constituent of the coating material, neither polymorphism nor separations occur, the stability of the release kinetics exists and the melting and solidification point of the mixture lies below 80° C.

So that undesired separation processes do not occur either before or after the HMC method, the coating material for the HMC method preferably consists of at least 98 percent by weight of polyglycerol fatty acid esters.

In contrast to already known coatings or coating agents, the proposed coating material is preferably free of solvents, which would have to be removed by evaporation after the coating of the disperse material in an energy-consuming and time-consuming drying step. It is also advantageous if the coating material does not have any surfactant additives, since in the case of such additives often the risk of undesired separations exists, which often only manifest themselves in ion-g-term studies relating to storage stability.

The use of the proposed coating material with polyglycerol fatty acid esters as the main component is not limited to the HMC method, as long as it is, by whatever method, brought by spraying its melt into a hollow spherical homeomorphic form, the inner cavity of which has disperse material described above, wherein the disperse material preferably has at least one active pharmaceutical ingredient. Surprisingly, it is also possible with the proposed coating material to coat crystals of one or more active pharmaceutical ingredients in a stable manner without the need of having to previously provide a granulate or agglomerates with one or more adjuvants.

A hot-melt coating method, in which disperse material is coated with a coating material of a composition according to one of claims 1 to 13, results in superior end products compared to the prior art, which are well adjustable in their release kinetics and also can be stored for longer periods of time without loss of quality. Thereby, such a hot-melt coating method is predestined to also provide at least one disperse material having a pharmaceutical active ingredient with a melt coating, in particular also such disperse material which has at least one thermolabile pharmaceutical active ingredient, wherein thermolabile here means that already after one hour's exposure above 100° C. the effective activity is reduced by 2%. 100% effective activity of a pharmaceutical active ingredient is present when all molecules of the pharmaceutical active ingredient are present in their active form or can be converted thereinto in vivo.

Surprisingly, it was possible to determine in the variation of parameters of the HMC method which are critical to the result, in particular the air inlet temperature, that this does not necessarily have to be 5° C. to 15° C. below the solidification temperature of the coating material for the proposed coating material, but rather, possibly due to the lower specific heat capacity of the proposed coating material compared to the prior art, can be brought up to 1° C. to 2° C. to this and thus effectively prevents the formation of undesired agglomerates during the spraying method.

In the following, it is explained in closer detail by means of illustrations and an example what properties the proposed coating material and combinations of the coating material and disperse material have and what parameters are to be taken into consideration in which way in a hot-melt coating method in which the proposed coating material is used.

595 g of $PG_4$ and 625 g of C18 fatty acid are placed in a glass apparatus with a distillation bridge and melted. The reaction is carried out under vacuum at 200° C. to 240° C. The esterification is carried out until an AN<1.0 mg KOH/g is reached.

Figure 1:
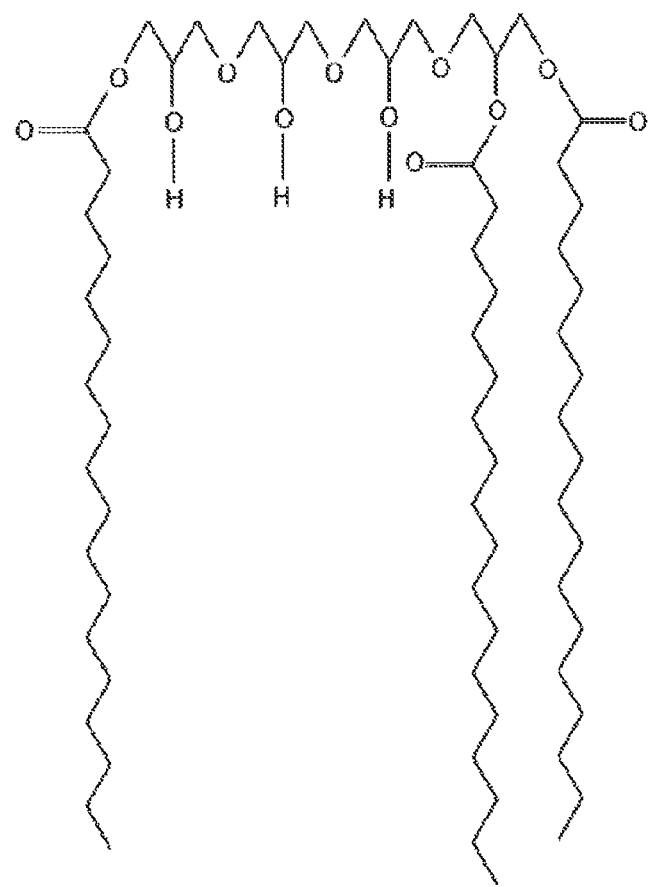
FIG. 1 illustrates a quantitative main structure showing a partial ester PG (4)-C18 synthesized by means of gas chromatography coupled with mass spectroscopy (GC-MS) according to one embodiment of the present disclosure.

The partial ester PG(4)-C18 synthesized as above shows in the examination by means of gas chromatography coupled with mass spectroscopy (GC-MS) the quantitative main structure shown in FIG. 1.

Figure 2:
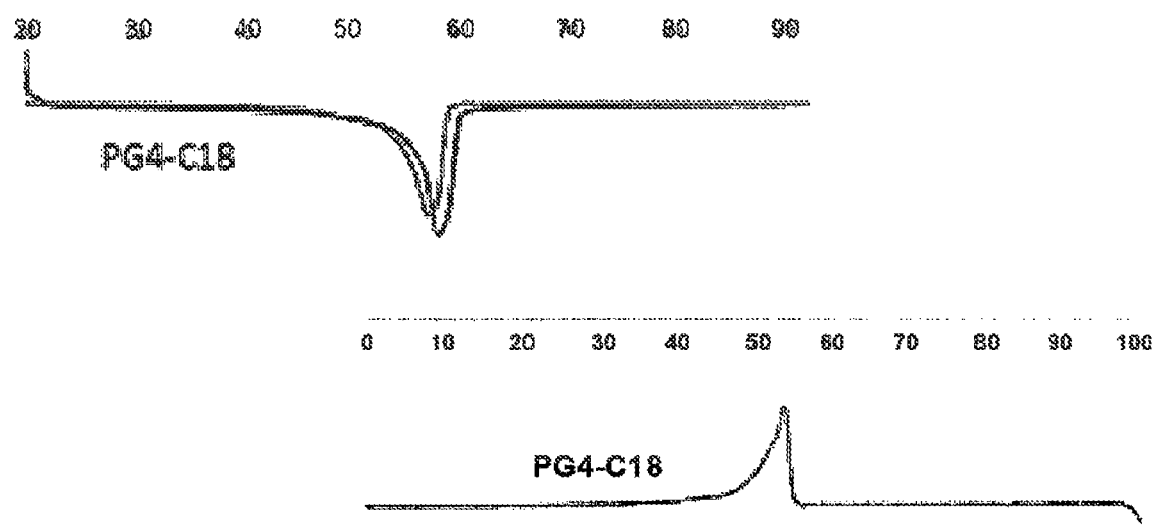
FIG. 2 illustrates the results of the examinations of PG(4)-C18 by means of dynamic differential calorimetry according to one embodiment of the present disclosure.

FIG. 2 shows the results of the examinations of PG(4)-C18 by means of dynamic differential calorimetry, wherein the temperature values on the X axis of the diagram are assigned to the heat flow in mW/g on the Y axis. The diagram on the left in FIG. 2 shows two almost congruent curves of two measurements of the partial ester PG(4)-C8, which respectively have exactly one endothermic minimum that can be assigned to the energy-consuming transition from the solid to the liquid phase on melting of the partial ester. The diagram on the right in FIG. 2 shows exactly one exothermic maximum for the partial ester PG(4)-C1n, which can be assigned to the energy-releasing transition from the liquid to the solid phase on solidifying of the partial ester. The measurements were carried out with a DSC 204 F1 Phoenix of Nietzsche Gerätebau GmbH, 95100 Selb, Germany. Here, a sample of 3-4 mg was weighed into an aluminum crucible and the heat flow was recorded continuously at a heating rate of 5K per minute. A second passage Was carried out at the same heating rate.

Figure 3:
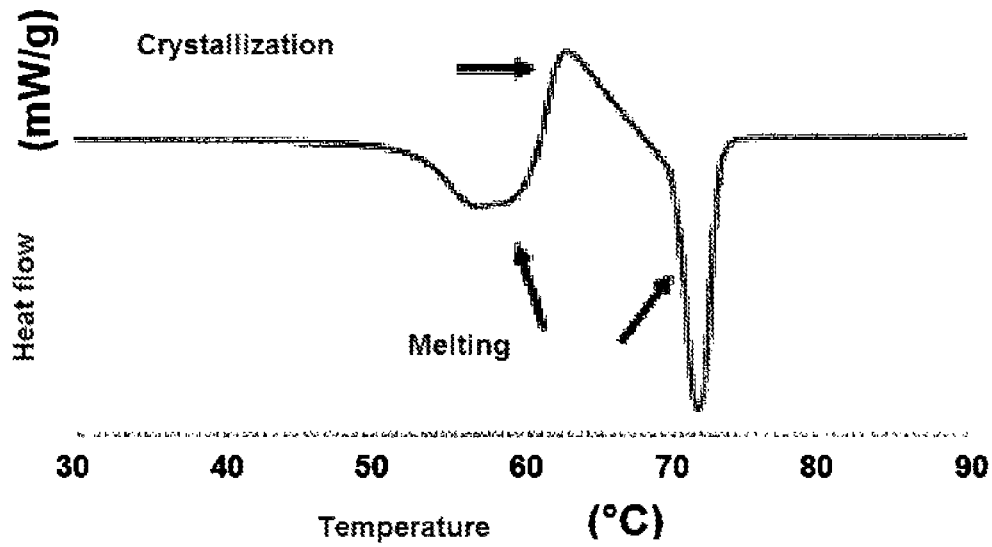
FIG. 3 illustrates a typical behavior of a polymorphic triacylglycerol during an examination by means of dynamic differential calorimetry when heating up according to one embodiment of the present disclosure.

FIG. 3 shows, as contrast to the desired behaviour of the polyglycerol fatty acid esters, the typical behaviour of a polymorphic triacylglycerol during an examination by means of dynamic differential calorimetry when heating up. Here, two local endothermic minima with an exothermic maximum lying therebetween can be seen, wherein the first endothermic, left-hand minimum occurs due to the melting of the unstable α-modification, followed by the exothermic maximum on the crystallization into the more stable ß-modification, which in turn melts on further temperature increase, recognizable by the second endothermic, right-hand local minimum.

Figure 4:
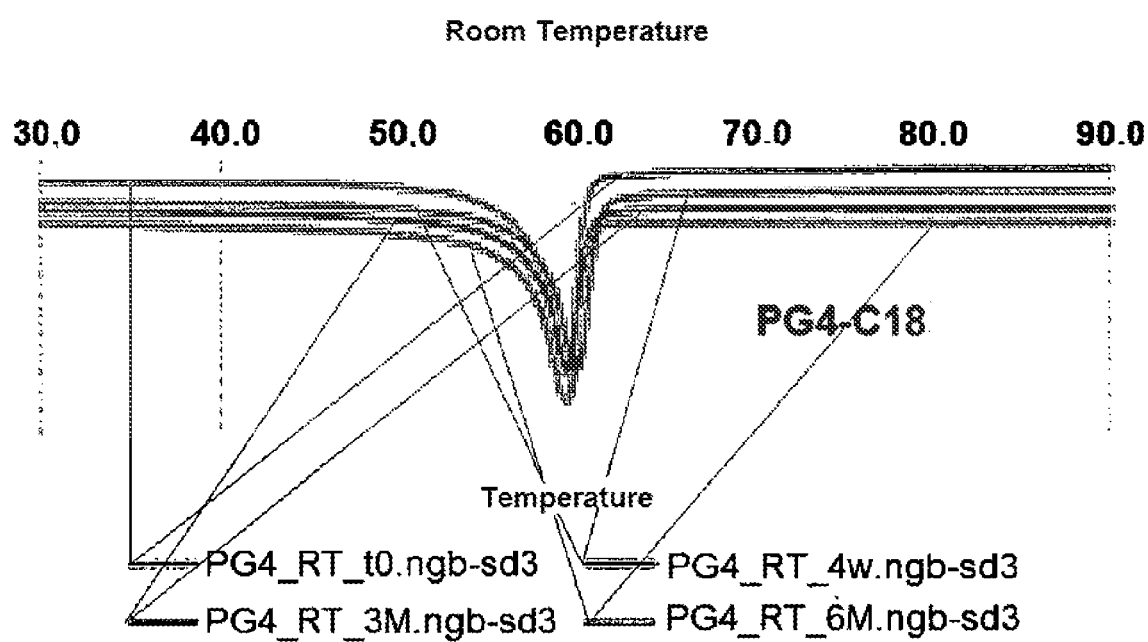
FIG. 4 illustrates a PG(4)-C18 partial ester examined by means of dynamic differential calorimetry on heating up after 6 months of storage at room temperature according to one embodiment of the present disclosure.
Figure 5:
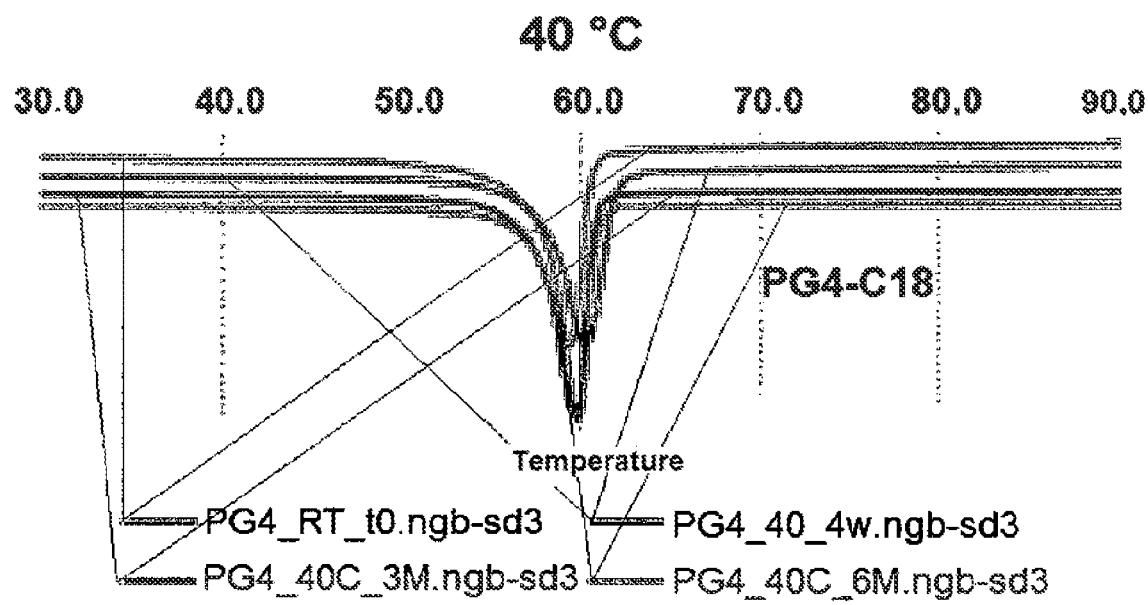
FIG. 5 illustrates a PG(4)-C18 partial ester examined by means of dynamic differential calorimetry on heating up after storage for 6 months at 40° C. according to one embodiment of the present disclosure.

FIG. 4 shows the PG(4)-C18 partial ester examined by means of dynamic differential calorimetry on heating up after 6 months of storage at room temperature. FIG. 5 shows the PG(4)-018 partial ester examined by means of dynamic differential calorimetry on heating up after storage for 6 months at 40° C. In both cases, there Is still no exothermic maximum to be seen that could indicate the crystallization into a more stable modification after melting.

For the WAXS and SAXS analyses, a point-focusing camera system, S3-MICRO, formerly Hecus X-ray Systems Gesmbh, 8020 Graz, Austria, now Bruker AXS GmbH, 76187 Karlsruhe, Germany, equipped with two linear position-sensitive detectors with a resolution of 3.3-4.9 angstroms (WAXS) and 10-1500 angstroms (SAXS) was used. The samples were introduced into a glass capilliary of approximately 2 mm in diameter, which was subsequently sealed with wax and placed in the capillary rotation unit. The individual measurements were exposed to an x-ray beam with a wavelength of 1.542 angstroms at room temperature for 1300 seconds.

Figure 6:
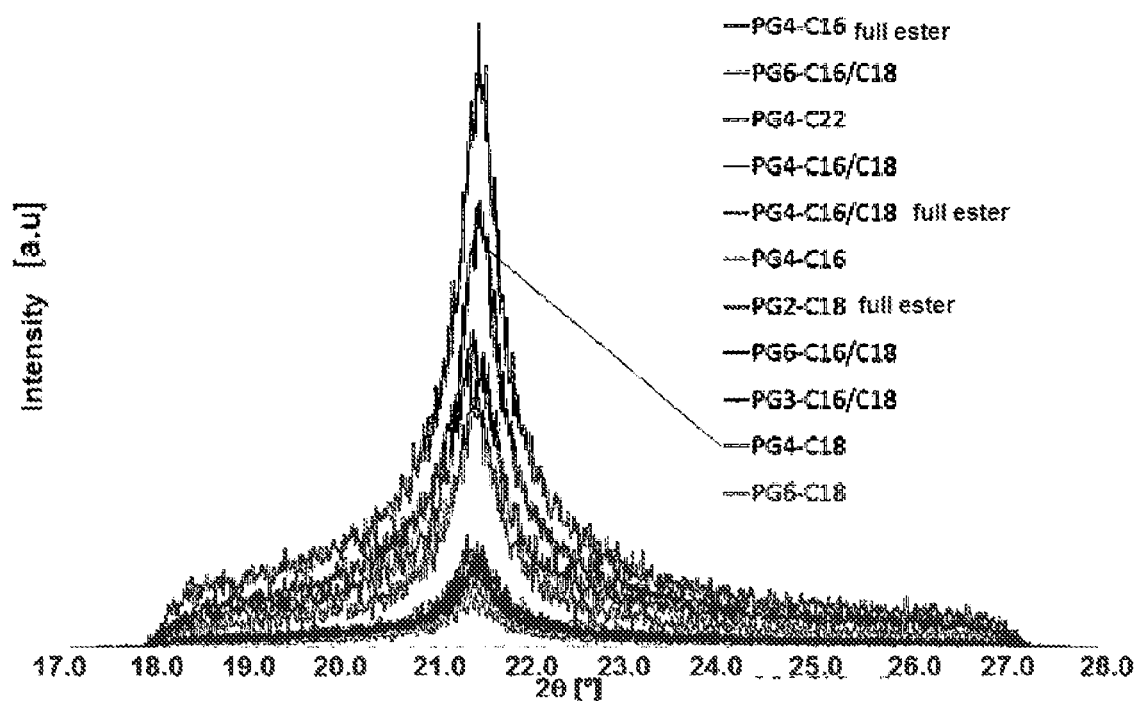
FIG. 6 illustrates results of a WAXS analysis of various polyglycerol fatty acid esters according to one embodiment of the present disclosure.
Figure 7:
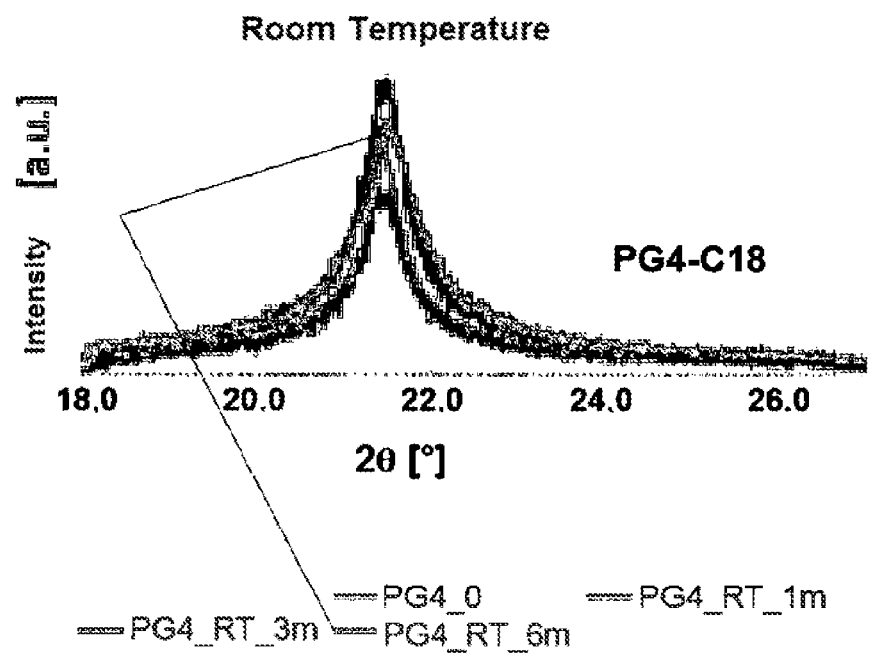
FIG. 7 illustrates results of a WAXS analysis of various polyglycerol fatty acid esters at an intensity maximum when stored for 6 months at room temperature according to one embodiment of the present disclosure.
Figure 8:
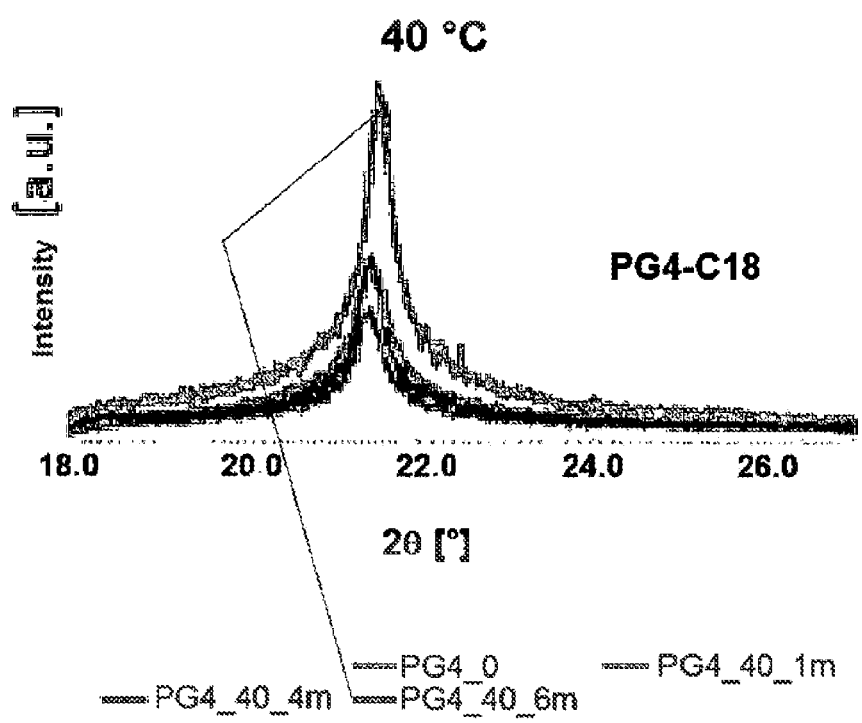
FIG. 8 illustrates results of a WAXS analysis of various polyglycerol fatty acid esters at an intensity maximum when stored for 6 months at 40° C. according to one embodiment of the present disclosure.

FIG. 6 shows the results of the WAYS analysis of various polyglycerol fatty acid esters including PG(4)-C18 partial esters (marked) below their solidification temperature, all of which show an intensity maximum at 2 θ of 21.4°. The Bragg angle corresponds to a distance of the network planes of 415 pm, which is typical for the lamellar packing of the α-modification. The intensity maximum remains stable both when stored for b months at room temperature, as shown in FIG. 7, and also when stored for 6 months at 40° C., as shown in FIG. 8.

Figure 9:
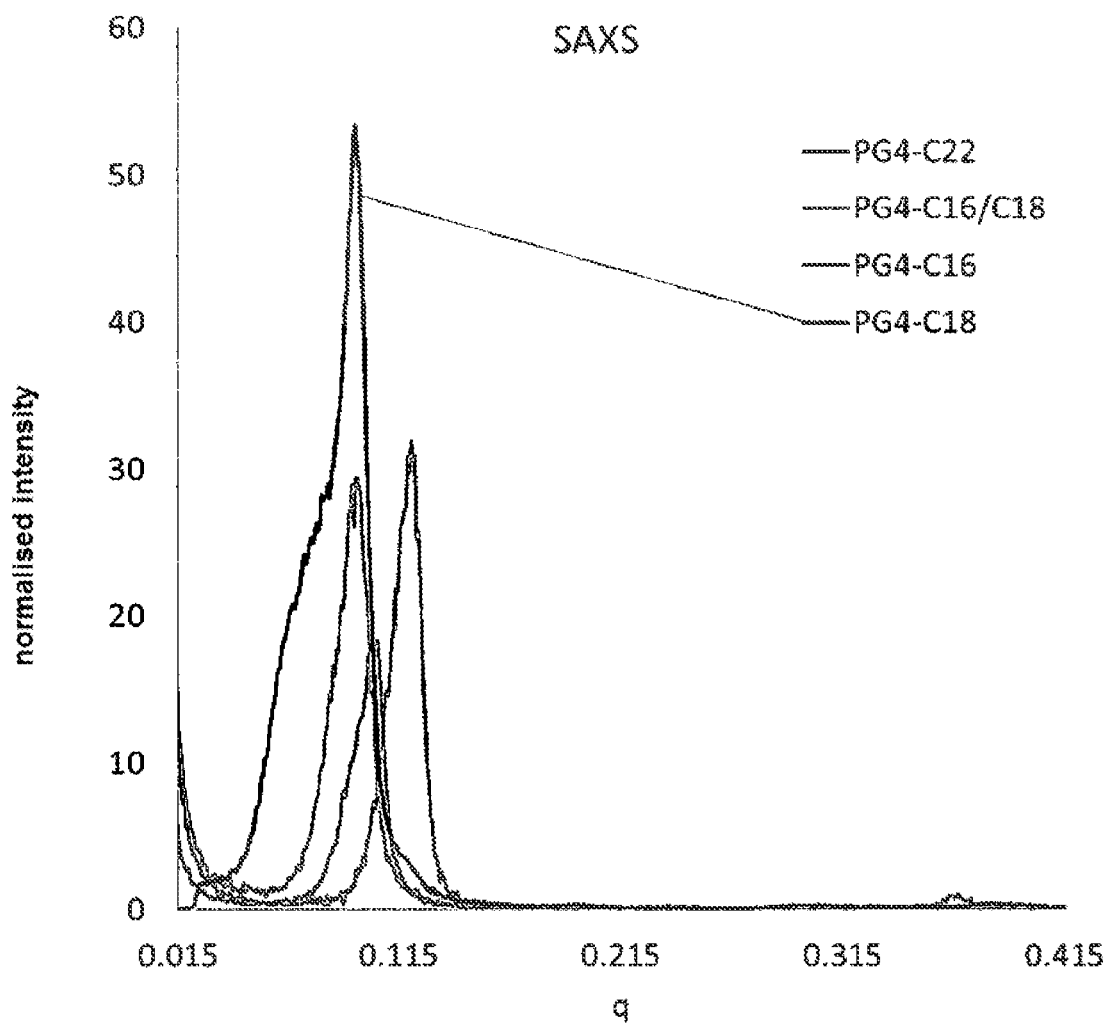
FIG. 9 illustrates results of a SAXS analysis of various polyglycerol fatty acid partial esters according to one embodiment of the present disclosure.

FIG. 9 shows the results of the SAXS analysis of various polyglycerol fatty acid partial esters. A lamellar distance of 65.2 angstroms can be derived for PG(4)-C18 partial esters. The thickness of the crystallites is 12.5 nm according to the Scherrer formula, with a Scherrer constant of 0.9, a wavelength of 1.542 angstroms, an FWHM value of 0.111 and a Bragg angle 3 of 0.047 (rad). The values of the SASX analysis of PG(4)-C18 partial esters also remained constant after six months of storage both at room temperature and also at 40° C. (not shown).

A rheometer Physica—Modular Compact Rheometer, MCR 300 of Anton Paar GmbH, 5054 Graz, Austria, was used for the measurement of the viscosity. The measurement was carried out on a CP-50-2 system with a conical plate with constant shear forces. Here, the sample was melted directly on the plate and the viscosity was determined at 80° C. and 100° C. The viscosity for PG(4)-C18 partial esters is accordingly 74.38 mPa·s at 80° C. and 34.46 mPa·s at 100° C. The partial ester can therefore be processed very well in a hot-melt coating method.

The evaluation of the dynamic differential calorimetry also allows statements about the solidification temperature of the PG(4)-C18 partial ester. The peak of the exothermic maximum on cooling of the sample rises between 53.4° C. and 57.0° C. with the maximum at 55.2° C., which marks the solidification temperature.

Figure 10:
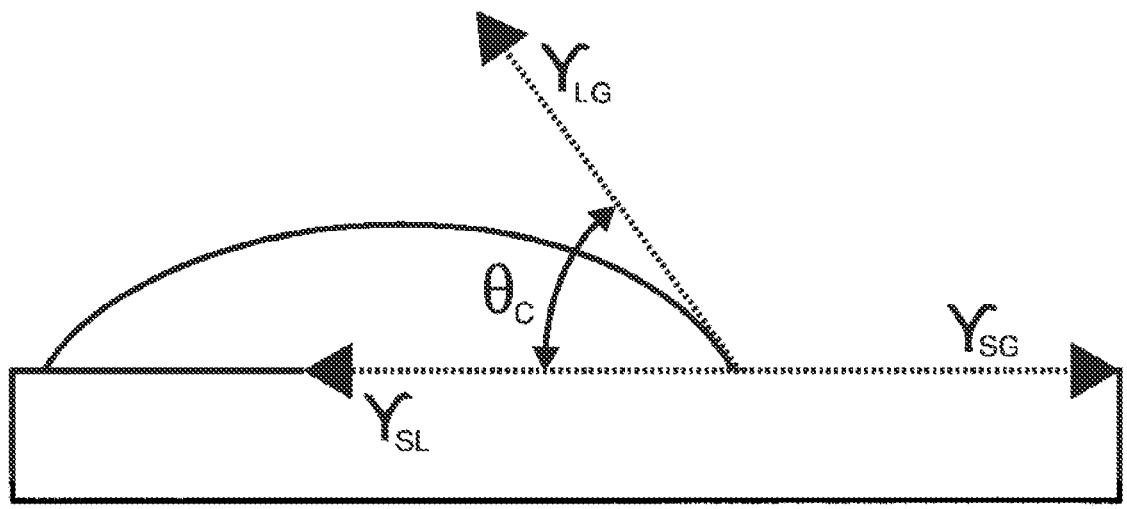
FIG. 10 illustrates a diagram which illustrates a measurement of a contact angle according to one embodiment of the present disclosure.

FIG. 10 shows a diagram which illustrates the measurement of the contact angle (cf. para. [0020]). For PG(4)-C18 partial esters, the contact angle is approximately 84°, which correlates with an HLB value of approximately 5.2. Compared to other polyglycerol fatty acid esters, PG(4)-C18 partial ester is to be assigned to the more hydrophilic polyglycerol fatty acid esters, as can be seen from FIG. 11 (there=PG4-C18), and thus suitable for the coating of active pharmaceutical ingredients for which an immediate release is desired because the HLB value at 5.2 lies above the HLB rapid release limit of about 4. FIG. 12 shows the change in the contact angle for PG(4)-C18 partial esters, middle diagram, compared to the start measurement (left column) after 16 weeks at room temperature (middle column) and after 16 weeks at 40° C. (right column). The contact angle does not change by more than 100, the hydrophobicity can thus be described as stable in comparison with monoglycerol fatty acid esters, such as tristearoylglycerol for example. The same applies to the PG3-C16/C18 partial esters also shown in FIG. 12, left diagram, and PG6-C18 partial esters, right diagram.

FIG. 13 shows the release kinetics for particles coated with PG(4)-C18 partial esters and alternatively with PG(3)-C16/C18 partial esters, each with 600 mg of N-acetylcysteine. The proportion of PG(4)-C18 partial ester was 45%, the proportion of PG(3)-C16/C18 partial ester was 50% of the total weight of the coated particles. The values on the Y-axis stand for the percentage proportions of the released N-acetylcysteine, the values on the X-axis for the time in minutes. The release investigations were carried out with a device that complies with USP-II, a DT820LH of ERWEKA GmbH, 63150 Heusenstamm, Germany, which has an automatic sample collector. The collected samples were analyzed by means of high pressure liquid chromatography, HPLC for short, under the following conditions: Column: Synergi Fusio RP 4 mm, 0 angstroms, 250 mm×4.6 mm; upstream column: Atlantis T3 (5 μm); mobile phase: acetonitrile 5%/water 95% (pH 1.6); Flow rate: 1 mL/min; In section volume: 20 mm; Column temperature: 21° C.; Temperature of the automatic sample collector: 5° C.; Wavelength: 220 nm; Running time: 20 min. The particles coated with PG(4)-C18 partial ester have an immediately releasing profile in which within the first 5 minutes less than 10% and within the first 30 minutes more than 85% of the N-acetylcysteine is released. In order to achieve a more effective taste masking, the HMC method used can in addition be carried out with a higher temperature of the inlet air used and higher spray rates in order to further reduce the release of the N-acetylcysteine within the first 5 minutes. The taste masking clue to the release kinetics of the particles coated with PG(3-C16/C18 partial ester can be designated as successful. Virtually no release takes place here in the first 5 minutes, which are critical for taste masking.

FIG. 14 shows the release kinetics of the N-acetylcysteine particles coated with PG(4)-C18 partial ester at the beginning, after one month, three months and five months of storage at 40° C. The release kinetics do not differ significantly, the product is stable.

FIG. 15 shows the release kinetics of the N-acetyl cysteine particles coated with PG(3)-C16/C18 partial ester at the beginning, after storage for one month at room temperature and after storage for one month at 40° C. The release kinetics do not differ significantly here either.

The successful taste masking by coating material having PG(3)-C16/C18 partial ester as main component was able to be achieved not least through the optimizing of the HMC method parameters. An Innojet Ventilus V-2.5/1 laboratory system served as coating device in combination with the Innojet hot melt device IHD-1 of Romaco Holding GmbH, 76227 Karlsruhe, Germany. PG(3)-C16/C18 partial ester was melted at 100° C. and sprayed onto N-acetylcysteine crystals with an average diameter of about 500 μm. The sample size for the HMC runs was respectively 200 g of disperse material. The spray rates and the air inlet temperatures were changed in the various HMC runs in order to determine the optimal setting for the coating. The effectiveness of the coating method was determined here according to the following equation: Effectiveness (%)=actual coating amount/theoretically achievable coating amount×100, wherein the actual coating amount is the percentage proportion of the coating material used in the respective HMC run applied onto the acetylcysteine crystals. At a spray rate of 5 g/min and an air inlet temperature of 35.0° C., the effectiveness was 90.7%. An increase of the air inlet temperature to 40° C. increased the effectiveness to 91.0%. Surprisingly, an increase of the spray rate to 7.5 g/min and of the air inlet temperature to 50° C. resulted ii an effectiveness of 100%. The two effectiveness values of 90.7% and 91.0% mean that 9.3 or respectively 9.0 percent by weight of the coating material are solidified before a spreading and distribution on the surface of the N-acetylcysteine crystals can take place. The solidified droplets, free of active ingredient, were collected as dust at the end of the respective run and weighed. In the case of 90.2% effectiveness it was 18.6 g, in the case of 91.0% effectiveness 13.0 g. The effectiveness of 100% was achieved here with an air inlet temperature of less than 2° C. below the solidification temperature of the coating material, in this case the PG(3)-C16/C18 partial ester, which has a solidification temperature of 51.7° C. The low specific heat capacity of the polyglycerol fatty acid esters used for the proposed coating material compared to conventional HMC coatings may be a reason why greater, advantageous flexibility in the setting of the air inlet temperature is now possible compared to the prior art. In the publication "Solvent-free melting techniques for the preparation of lipid-based solid oral formulations", K. Becker et al. in Pharmaceutical Research, May 2015, 32(5), 1519-45, air inlet temperatures of 5° C. to 15° C. below the solidification temperature of the HMC coating material are still considered essential.

In contrast to the release tests with coating material having PG(4)-C18 partial ester, to determine the release kinetics of the N-acetylcysteine crystals coated with PG(3)-C16/C18 partial ester, instead of an automatic sample collector an integrated detection for UV radiation/visible light was used with a Lambda 25 spectrometer of Perkin Elmer Inc., Waltham, Massachusetts, USA. The release tests were carried out at 37° C. in 900 mL of ultrapure water, obtained from Merck KGaA, Darmstadt, Germany, at a paddle stirring speed of 100 revolutions per minute. The release profiles were initially set to 0% and scaled to 100% release for the release level at the end of the release. FIG. 16 shows the release curves for the particles coated with an air inlet temperature of 35° C., 40° 0 and 50° C. in the HMC method. The particles coated a 50° C. with an effectiveness of 100% have virtuality no release of N-acetylcysteine within the first 5 minutes. The HMC method used with the coating material having PG(3)-C16/C18 partial ester as the main component is therefore well suited for taste masking, after optimization of the air inlet temperature, which is surprisingly possible with the proposed coating material in this way.

The invention claimed is:

1. A hot-melt coating method, in which disperse material, dispersed in a gas or gas mixture and being provided as a fluidized bed, is coated with a coating material by spraying the disperse material with the coating material to form a product from individual surface stable parts,
  characterized in that
  the coating material consists of a composition with at least 98 percent by weight on one or more polyglycerol fatty acid esters each obtainable by complete or partial esterification of a linear or branched polyglycerol containing two to eight glycerol units with one or more fatty acid, each containing 6 to 22 carbon atoms, as the main constituent by weight, wherein the gas or gas mixture has a temperature during the spraying which is only 1° C. to 3° C. below the solidification temperature of the coating material.

2. The hot melt coating method as claimed in claim 1, characterized in that
  the fatty acids on which the polyglycerol fatty acid ester or polyglycerol fatty acid esters of the coating material are based are saturated or unbranched or both saturated as well as unbranched.

3. The hot melt coating method as claimed in claim 1, characterized in that
  the fatty acids on which the polyglycerol fatty acid ester or polyglycerol fatty acid esters of the coating material are based contain 16, 18, 20 or 22 carbon atoms.

4. The hot melt coating method as claimed in claim 1, characterized in that
  the examination of the polyglycerol fatty acid ester or individual polyglycerol fatty acid esters of the coating material using heat flux differential scanning calorimetry produces, upon heating up, respectively only one endothermic minimum and upon cooling down, respectively only one exothermic maximum.

5. The hot melt coating method as claimed in claim 1, characterized in that
  the polyglycerol fatty acid ester or polyglycerol fatty acid esters of the coating material have a stable subcellular form below their solidification temperature with a substantially constant lamellar distance at 40° C. for at least 6 months according to an evaluation of the Bragg angle determined by means of WAXS analysis.

6. The holt melt coating method as claimed in claim 1, characterized in that
  the polyglycerol fatty acid ester or polyglycerol fatty acid esters of the coating material have a stable subcellular form below their solidification temperature, with a substantially constant thickness of the lamellar-structured crystallites over at least 6 months at 40° C. according to SAXS analysis evaluated using the Scherrer equation.

7. The hot melt coating method as claimed in claim 1, characterized by
  at least one polyglycerol fatty acid ester of the coating material from the following group:
    PG(2)-C18 full esters, PG(2)-C22 partial esters with a hydroxyl value of 15 to 100, PG(2)-C22 full esters, PG(3)-C16/C18 partial esters with a hydroxyl value of 100 to 200, PG(3)-C22 partial esters with a hydroxyl value of 100 to 200, PG(3)-C22 full esters, PG(4)-C16 partial esters with a hydroxyl value of 150 to 250, PG(4)-C16 full esters, PG(4)-C16/C18 partial esters with a hydroxyl value of 150 to 250, PG(4)-C16/C18 full esters, PG(4)-C18 partial esters with a hydroxyl value of 100 to 200, PG(4)-C22 partial esters with a hydroxyl value of 100 to 200, PG(6)-C16/C18 partial esters with a hydroxyl value of 200 to 300, PG(6)-C16/C18 full esters, PG(6)-C18 partial esters with a hydroxyl value of 100 to 200, wherein in the polyglycerol fatty acid esters containing two fatty acid residues which are different because of the number of their carbon atoms, those with the lower number are present in an amount of 35% to 45%, those with the higher number are present in a complementary amount of 55% to 65%, and the full esters listed above have a hydroxyl number less than 5.

8. The hot melt coating method as claimed in claim 1, characterized by
  a viscosity of the polyglycerol fatty acid ester or polyglycerol fatty acid esters of the coating material of less than 300 mPa s at 80° C.

9. The holt melt coating method as claimed in claim 1, characterized by
  a solidification temperature of the polyglycerol fatty acid ester or individual polyglycerol fatty acid esters of the coating material which is below 75° C.

10. The hot melt coating method as claimed in claim 1, characterized in that
  the contact angle of the polyglycerol fatty acid ester or individual polyglycerol fatty acid esters of the coating material as a measure of the hydrophobicity differs by less than 10° from the starting value after 16 weeks at 40° C. as well as at 20° C.

11. The hot melt coating method as claimed in claim 1, characterized by
  a post-synthetic mixture of polyglycerol fatty acid esters as the main constituent of the coating material by weight which can be obtained from esterification reactions which respectively differ from one another due to the reaction partners employed.

12. The hot melt coating method as claimed in claim 1, characterized by
  a solvent-free or surfactant-free or both solvent-free as well as surfactant-free composition for the coating material.

13. The hot melt coating method as claimed in claim 1, characterized in that
  the disperse material comprises at least one active pharmaceutical ingredient.

14. The hot melt coating method as claimed in claim 1, characterized in that
  the disperse material consists of crystals of one or more active pharmaceutical ingredients.

15. The hot melt coating method as claimed in claim 13 or claim 14,
  characterized in that
  at least one of the active pharmaceutical ingredients is thermolabile and, after coating and subsequent cooling to room temperature, has more than 98% of its original effective activity.

* * * * *